United States Patent
Zielinski

(10) Patent No.: US 6,699,900 B2
(45) Date of Patent: Mar. 2, 2004

(54) HYDROPHILIC AND LIPOPHILIC SILIBININ PRO-FORMS

(76) Inventor: Jan E. Zielinski, 7396 Trade St., San Diego, CA (US) 92121

(*) Notice: Subject to any disclaimer, the term of this patent is extended or adjusted under 35 U.S.C. 154(b) by 116 days.

(21) Appl. No.: 10/110,120

(22) Filed: Apr. 5, 2002

(65) Prior Publication Data

US 2003/0069302 A1 Apr. 10, 2003

Related U.S. Application Data

(60) Provisional application No. 60/282,052, filed on Apr. 7, 2001.

(51) Int. Cl.$^7$ ............................................. A61K 31/335
(52) U.S. Cl. ...................................... 514/452; 549/362
(58) Field of Search ......................... 514/452; 549/362

*Primary Examiner*—Amelia Owens
(74) *Attorney, Agent, or Firm*—Harris Brotman, Procopio, Cory, Hargreaves & Savitch LLP

(57) ABSTRACT

Hydrophilic and lipophilic silibinin pro-forms and pharmaceutical compositions thereof, and methods of using compositions of silibinin pro-forms for topical or oral administration for treatment of disorders of cell proliferation, oxidative stress, sebaceous gland activity, and cardiovascular activity.

18 Claims, 1 Drawing Sheet

FIGURE 1: SILIBININ
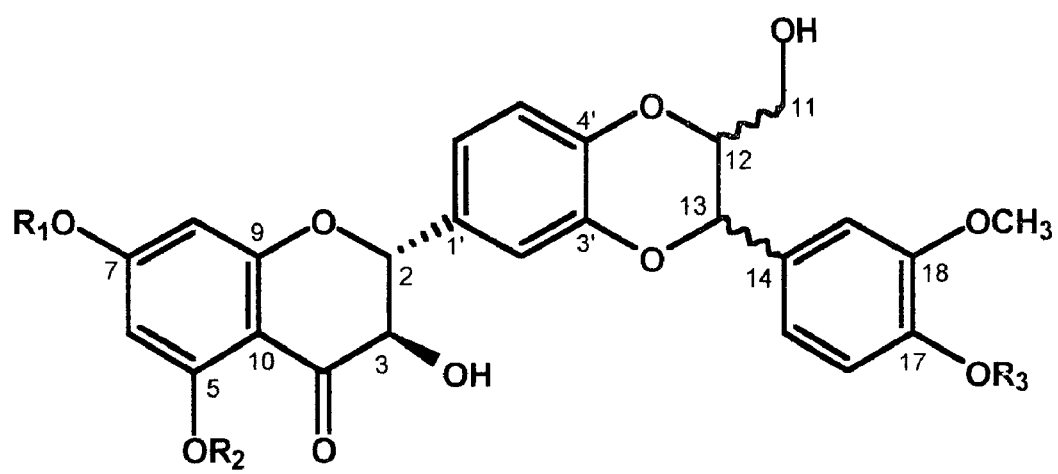

HYDROPHILIC AND LIPOPHILIC SILIBININ PRO-FORMS

This application claims the benefit of Provisional application Ser. No. 60/282,052, filed Apr. 7, 2001.

BACKGROUND OF THE INVENTION

1. Field of the Invention

This invention relates generally to the field of flavonoids, and more specifically to forms of flavonoids that possess increased bioavailability for nutritional, pharmaceutical and cosmetic applications.

2. Description of Related Art

References to the publications and other reference materials to describe the backgound of the invention and to provide additional detail regarding its practice are hereby incorporated by reference. For convenience, the reference materials are numerically referenced and grouped in the appended bibliography.

Silymarin, a polyphenolic flavonoid mixture isolated from milk thistle, *Silybum marianum* (L.) Gaertn, is composed mainly of three isomers: silidianin, ilichristin and the major component, silibinin. Silymarin components are in a unique class of natural products, known as flavonolignans, produced in the plant by radical coupling of dihydroquercetin and coniferyl alcohol. Silibinin (see FIG. 1, where $R_1=R_2=R_3=H$) has been found to exist as a mixture of two diastereomers (1) (2R, 3R, 12S, 13S and 2R, 3R, 12R, 13R). In general, it has been shown that the biological activities of Silymarin are associated with the major component, silibinin (2, 3). Silibinin also is known as silybin.

Silymarin is commonly used as a nutritional supplement. It has been shown to protect the liver against the negative effects of toxins present in food, air and water. In general, silymarin is used to restore normal liver function (4).

Silibinin has been found to possess a wide variety of biological activities, including hepato-protection (5) and inhibition of breast (6), prostate (7) and skin (8) tumor development.

Previous investigations of the application of silibinin and/or silymarin on the skin have demonstrated inhibition of photocarcinogenesis (9), inhibition of inflammation (10), reversal of skin aging (11, 12, 13) and treatment of dermatological conditions, like psoriasis and dermatitis (14). Silymarin also has been found to stimulate hair regrowth (15).

Previous studies have relied on the use of silymarin as extracts that typically are standardized on the amount of silibinin present. In general, the use of extracts creates a number of problems. For example, the composition of the extract usually is not completely determined, resulting in uncertainty in the relationship of chemical components and their biological activities. Furthermore, unidentified components present in extracts might cause negative side effects.

In general, it is well known that silymarin and silibinin are not readily soluble in aqueous or lipophilic phases (Merck Index, Reference 8680). Furthermore, once they reach the bloodstream, then they are readily metabolically transformed to glucuronide and sulfate conjugates, and cleared in the urine. Both of these properties result in poor bioavailability of silibinin or silymarin, thereby limiting their effectiveness.

One strategy for enhancing the absorption of silibinin is to convert silibinin into lipophilic complexes with phospholipids (16). Another approach involves the chemical modification of silibinin to form the 3,11-dihemisuccinate salt of silibinin (17).

DISCLOSURE OF THE INVENTION

The present invention provides hydrophilic and lipophilic pro-forms of silibinin. The hydrophilic pro-forms have the formula In this formula, one or more of R1, R2, and R3 are independently selected from the group consisting of cationic esters, anionic esters, neutral esters, and H.

Pharmaceutical compositions of the hydrophilic pro-forms of silibinin are suitable for topical or oral administration in an individual. The pharmaceutical composition includes a hydrophilic silibinin pro-form and a pharmaceutically acceptable carrier.

In another aspect, the invention is directed to lipophilic pro-forms of silibinin. The lipophilic pro-forms have the formula wherein
  one or more of R1, R2, and R3 are independently selected from the group consisting of aliphatic acid residues, aromatic acid residues, and H.

Pharmaceutical compositions of the lipophilic pro-forms of silibinin are suitable for topical or oral administration in an individual. The pharmaceutical composition includes a lipophilic pro-form of silibinin and a pharmaceutically acceptable carrier.

Other features of the invention are directed to methods of treating a subject having or at risk of having a cell proliferative disorder by administering to the subject a therapeutically effective amount of a silibinin pro-form, hydrophilic form or lipophilic form depending on the indication, which include breast cancer, skin cancer, uterine cancer, testicular cancer, lung cancer, prostate cancer, and liver cancer. Another method of the invention is directed to decreasing oxidative stress in a subject having a disorder associated with oxidative stress by administering to the subject a therapeutically effective amount of a silibinin pro-form.

The above-discussed and many other features and attendant advantages of the present invention will become better understood by reference to the following detailed description of the invention taken in conjunction with the accompanying drawing.

BRIEF DESCRIPTION OF THE DRAWING

FIG. 1 is the chemical formula of silibinin; $R_1$, $R_2$, and $R_3$ are H.

MODES OF CARRYING OUT OF THE INVENTION

General Description and Definitions

The practice of the present invention will employ, unless otherwise indicated, conventional biochemistry, medicinal chemistry, and organic chemistry. Techniques are fuly explained in the literature. See e.g. *Biochemistry*, 4$^{th}$ edition, Lubert Stryer, W. H. Freeman, 1975; *Harper's Biochemistry*, 21$^{st}$ edition, H. A. Harper and R. K. Murray, Appleton & Lange, 1988); (*Medicinal Chemistry: The Role of Organic Chemistry in Drug Research*, (eds) S. M. Roberts and B. J. Price, Academic Press, 1985; *Comprehensive Medicinal Chemistry: the Rational Design, Mechanistic Study and Therapeutic Application of Chemical Compounds*, (eds) C. Hansch, P. G. Sammer and J. b. Taylor, V. 1–6, 1990); *Organic Chemistry: Reactions and Mechanisms*, Bernard Miller, Prentice Hall, 1998; *Advanced Organic Chemistry: Reactions, Mechanisms and Structure*, 4$^{th}$ edition, Jerry Marsh, Wiley, 1992).

The strategy adopted herein was to produce lipophilic or hydrophilic pro-forms of Silibinin by covalent modifications of the phenolic groups at C-5, C-7 or C-17. The resulting pro-forms demonstrated improved bioavailability. These pro-forms under physiological conditions, either spontaneously or enzymatically, were hydrolyzed to the parent compound. The derivatives are of the general formula of Silibinin pro-forms as shown in the FIG. 1.

A "hydrophilic Silibinin pro-form" is a compound of the formula indicated in FIG. 1 wherein:

For the mono-substituted form:
One of $R_1$, $R_2$ or $R_3$ is a cationic, anionic or neutral ester, with the remaining as H.

For the di-substituted form:
Two of $R_1$, $R_2$ or $R_3$ are cationic, anionic or neutral esters, with the remaining as H.

For the tri-substituted form:
$R_1$, $R_2$ and $R_3$ are cationic, anionic or neutral esters.

Accordingly, hydrophilic pro-forms of silibinin in the present invention are represented by the formula of FIG. 1, wherein one or more of $R_1$, $R_2$, and $R_3$ are independently selected from the group consisting of cationic esters, anionic esters, neutral esters, and H Examples of cationic esters include, but are not restricted to chloride, phosphate and sulfate containing salts of an amino acid or polyamino acid residue. Examples of anionic ester include, but are not restricted to organic and inorganic salts of phosphoric or sulfuric acid residue; and esters containing in the residue aliphatic or aromatic carboxylic group or carboxylic groups. Examples of a neutral ester include but are not restricted to a residue from the group known as polyoxyethylene acids.

A "lipophilic/silibinin pro-form" is a compound of the general formula indicated in FIG. 1 wherein:

For the mono-substituted form:
One of $R_1$, $R_2$ or $R_3$ is an aliphatic or aromatic acid residue, with remaining as H.

For the di-substituted form:
Two of $R_1$, $R_2$ or $R_3$ are aliphatic or aromatic acid residues, with remaining as H.

For the tri-substituted form:
$R_1$, $R_2$ and $R_3$ are aliphatic or aromatic acid residues.

Accordingly, lipophilic pro-forms of silibinin in the present invention are represented by the formula of FIG. 1, wherein one or more of $R_1$, and $R_2$, and $R_3$ are independently selected from the group consisting of aliphatic acid residues, aromatic acid residues, and H.

Examples of aliphatic ester include those of saturated or unsaturated, linear or branched, carboxylic residue having from 2 to 30 carbon atoms or an aliphatic ester composed of saturated or unsaturated, linear or branched, carboxylic residue having from 2 to 30 carbon atoms substituted with oxygen, sulfur or nitrogen functional groups. In a preferred form, the esters are saturated or unsaturated fatty acid residues having from 10 to 30 carbon atoms.

Examples of an aromatic ester include, but are not restricted to benzoic acid residue, benzoic acid residue substituted with oxygen, sulfur or nitrogen functional groups or aliphatic acid residue substituted with phenyl or oxygen, sulfur or nitrogen substituted phenyl groups.

In various embodiments of the pro-forms of silibinin in the present invention, hydroxyl groups at 5, 7 and 17 positions of silibinin are converted to hydrophilic or lipophilic derivatives. Under physiological conditions as a result of enzymatic or spontaneous hydrolysis, these pro-forms are hydrolyzed into free silibinin. Kinetics of this process can be controlled by use of appropriate formulations of the pro-forms so as to diminish metabolic transformation and enhance the absorption of silibinin through the skin.

Selected pro-forms of silibinin were prepared in a cosmetically and pharmaceutically acceptable formulation and tested for their effectiveness in hair care. It was observed that topical application of both lipophilic and hydrophilic pro-forms of silibinin improved the regrowth of hair for male individuals regardless of age. In addition, application of lipophilic and hydrophilic pro-forms of silibinin restored the color of the hair and improved the structure of the hair. The use of these selected silibinin pro-forms offers a means to improve hair care without the need to use substances with anti-androgenic activity, which are associated with undesirable side effects.

The general procedure for the synthesis of lipophilic silibinin esters is based on acylation of phenolic groups at C-5, C-7 and C-17 by using appropriate acid chlorides in the presence of amine (e.g., pyridine, diisopropylethylamine) in aprotic solvent (e.g., dioxane). The yield of mono-, di- or tri-substituted silibinin pro-forms is a function of the molar ratio of the appropriate acid chloride to silibinin. The reaction mixture was mixed with water and the crude product was extracted with ethyl acetate. After evaporation of the solvent, the residue was separated by using silica gel flash chromatography and then with HPLC. Identification of the products was established by using electro-spray mass spectroscopy and $^1$H-NMR.

The procedure to synthesize silibinin phosphate pro-forms (anionic pro-form) is based on the use of the phosphotriester approach (18, 19). Two well known phosphorylating agents are dibenzyldiisopropylphosphoramidate and di-tert-butyl diisopropylphosphoramidate in the presence of 1H,5-methyltetrazole demonstrate regio-selective esterification of silibinin phenolic groups. In the case of the use of di-tert-butyl diisopropylphosphoramidate, silibinin-7-phosphate was the main product in contrast to dibenzyldiisopropylphosphoramidate, which generates silibinin-17-phosphate as the main component. The yield of mono-, di- or tri-phosphate silibinin pro-forms is a function of the molar ratio of the phosphorylating agents, catalyst and silibinin. Synthesis of the target compounds was based on the selective phosphorylating properties of these phosphorylating reagents. Following the phosphorylation reaction, the desired products were isolated by using HPLC purification and identified by electro-spray mass spectroscopy and $^1$H-NMR. Conversion of silibinin dibenzylphosphates to silibinin phosphates resulted from hydrogenlysis by using hydrogen in the presence of palladium catalyst. Conversion of silibinin tert-dibutylphosphates to silibinin phosphates resulted from treatment with 30% trifluoroacetic acid in acetic acid at room temperature. Purity of the final compounds in form of sodium salts of silibinin phosphates was established by electro-spray mass spectroscopy and $^{31}$P-NMR.

The procedure to synthesize silibinin cationic pro-forms was based on the use of a protected form of the appropriate amino acid, made by converting the amino group to benzyl carbamate derivative, followed by conversion to the acid chloride form by using oxalyl chloride. This activated carboxylic group was reacted with silibinin in the presence of amine (e.g., pyridine, diisopropylethylamine) in aprotic solvent (e.g., dioxane). The yield of mono-, di- or tri-substituted silibinin pro-forms is a function of the molar ratio of the selected acid chloride reagent and silibinin. Silibinin cationic pro-forms were generated by deprotection of the amino group by using hydrogen on palladium-charcoal as a catalyst and conversion to an inorganic salt form (e.g., hydrochloride, sulfate). Purity of the product was assessed by HPLC, electro-spray mass spectroscopy and $^1$H-NMR.

The neutral, hydrophilic silibinin pro-form was synthesized by converting an appropriate polyoxyethylene carboxylic acid to the acid chloride form by using oxalyl chloride prior to reaction with silibinin in the presence of amine (e.g., pyridine, diisopropylethylamine) in aprotic solvent (e.g., dioxane). The yield of mono-, di- or tri-substituted silibinin pro-forms is a function of the molar ratio of the selected acid chloride reagent and silibinin. Purity of the product was assessed by HPLC, electro-spray mass spectroscopy and $^1$H-NMR.

Practice of the synthetic methods resulted in the generation of mono-, di-, and tri-substituted derivatives of silibinin. Mono-substituted silibinin derivatives at C-7 are the preferred embodiment.

Therapeutic or Prophylactic Compositions of Silibinin Pro-Forms

In other aspects of the invention, the pro-compounds may adventageously be employed therapeutically or prophylactically for variety conditions, provided as a dietary supplement, drug or bioactive component of cosmetics.

Pharmaceutical Compositions

The invention also contemplates various pharmaceutical compositions containing a silibinin pro-form that are effective in treating a variety of disorders. These disorders include "cell proliferative disorders", "disorders associated with oxidative stress", "skin disorders", and "cardiovascular disorders".

The term "neoplasia" refers to a disease of inappropriate cell proliferation. This derangement is most evident clinically when tumor tissue bulk compromises the function of vital organs. The term "cell proliferative disorder" denotes malignant as well as nonmalignant cell populations which often appear to differ from the surrounding tissue both morphologically and genotypically. Malignant cells (i.e., tumors or cancer) develop as a result of a multistep process. Concepts describing normal tissue growth are applicable to malignant tissue because normal and malignant tissues can share similar growth characteristics, both at the level of the single cell and at the level of the tissue. Tumors are as much a disease of disordered tissue growth regulation as of disordered cellular growth regulation. The growth characteristics of tumors are such that new cell production exceeds cell death; a neoplastic event tends to produce an increase in the proportion of stem cells undergoing self-renewal and a corresponding decrease in the proportion progressing to maturation (McCulloch, E. A., et al, 1982, "The contribution of blast cell properties to outcome variation in acute myeloblastic leukemia (AML)," Blood 59:601–608). In one embodiment, the cells treated by the method id the invention are neoplastic cells.

The term cardiovascular disorder refers to any coronary or cardio-circular disease, including atherosclerosis and hypercholesterolemia.

The term "disorder associated with sebaceous gland activity" refers to a disorder of the pilosebaceous glands of the mammalian skin and scalp. Examples aredisorders of sebum secretin such as acne. "Acne" is a pilosebaceous disease characterized by comedo, papules, inflamed nodules and superficial pus-filled cysts. The course and the severity of the disease is determined by the interaction between hormones, keratinization, sebum formation and bacteria. The term "treating sebaceous gland activity", as used in herein means preventing, retarding, and/or arresting the production of sebum. The term "treating acne" refers to preventing, retarding, and/or arresting the process of acne formation.

The pharmaceutical compositions according to the invention are prepared by bringing a pro-form of silibinin of the present invention into a form suitable for administration (e.g., pharmaceutically acceptable carrier) to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences*, 15$^{th}$ ed. Easton: Mack Publishing Co., 1405–1412, 1461–1487, 1975, and *The National Formulary XIV.*, 14$^{th}$ ed. Washington: American Pharmaceutical Association, 1975, the contents of which are hereby incorporated by reference. The pH and exact concentration of the various components of the pharmaceutical composition are adjusted according to routine skills in the art. See *Goodman and Gilman's The Pharmacological Basis for Therapeutics*, 7$^{th}$ ed.

In another embodiment, the invention relates to a method of treating a cell proliferative disorder, a disorder associated with oxidative stress, a disorder, and a cardiovascular disorder. These methods involves administering to a subject a therapeutically effective dose of pharmaceutical composition containing the compounds of the present invention and a pharmaceutically acceptable carrier. "Administering" the pharmaceutical composition of the present invention may be accomplished by any means known to the skilled artisan. By "subject" is meant any mammal, preferably a human.

The pharmaceutical compositions are preferably prepared and administered indose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form if an individual does unit or else several smaller dose units and also by multiple administration of subdivided doses at specific intervals.

The dosage should not be so large as to cause adverse side effects, such as unwanted cross reactions, anaphylactic reactions and the like, Generally, the dosage will very with the age, condition, sex, and extent of the disease in the patient and can be determined by one skilled in the art. The dosage can be adjusted by the individual physician in the event of any contraindications and can be readily ascertained without resort or undue experimentation.

The pharmaceutical compositions according to the invention are in general administered topically, intravenously, orally, or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation, excipients and additives and/or auxiliaries such as disintegrants, binders, coating agents, swelling agents, lubricants, flavorings, sweeteners or solubilizers are customarily used as discribed above. The pharmaceutical compositions are suitable for use in a variety of drug delivery systems. For a brief review of present methods for drug delivery, see Langer, Science, 249:1527–1533, 1990, which is incorporated herein by reference.

The pharmaceutical compositions according to the invention may be administered locally or systematically. By "therapeutically effective dose" is meant the quantity of a compound according to the invention necessary to prevent, cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman and Gilman's: the Pharmacological Basis of Therapeutics*, 8$^{th}$ ed., Pergamon Press, 1990; and *Remington's Pharmaceutical Sciences*, 17$^{th}$ ed., Mack Publishing Co., Easton Pa., 1990, each of which is herein incorporated by reference. Effectiveness if the dosage can be monitored methods well known to one of ordinary skill in the art.

EXAMPLE 1

Silibinin-7-palmitate

A solution of palmitoyl chloride (0.7 ml, 2.03 mmol) in dioxane (2 ml) was added dropwise to a vigorously stirred suspension of silibinin (1 g, 2.07 mmol) and diisopropylethylamine (1.2 ml, 7 mmol) in dioxane (15 ml) at 0° C. The mixture, while stirring, was allowed to reach room temperature (30 min.) and then poured into ice water. The reaction product was extracted with ethyl acetate. The organic layer was washed with 1% sodium carbonate, 1% hydrochloric acid, water, dried over anhydrous $Na_2SO_4$ and the solvent removed under reduced pressure. The crude products were separated by HPLC on an ODS-2 column using methanol as a solvent, detected at 280 nm. The main product was collected and after evaporation of solvent, crystallized from ethyl acetate/hexane. Obtained: 0.82 g (52% yield) of silibinin-7-palmitate.

Spectroscopic Data of Silibinin-7-palmitate

Electro-spray mass spectrum in the negative scan showed: m/z 719 [M–H]. $^1$H-NMR (500 MHz, DMSO-d$_6$) δ: 0.845 (t, 3H, J=6.5 Hz), 1.227–1.309 (br, 24H), 1.597 (m, 2H, J=7.3 Hz), 2.541 (t, 2H, J=7.3 Hz), 3.547 (ddd, 1H, J=1.8, 1.8 and 10.4 Hz), 3.778 (s, 3H), 4.171 (m, 1H), 4.767 (m, 1H, J=5.8 Hz), 4.915 (d, 1H, J=7.9 Hz), 4.950 (t, 1H, J=5.2 Hz), 5.225 (d, 1H, J=11.5 Hz), 5.956 (d, 1H, J=6.3 Hz), 6.302 (d, 1H, J=2.7 Hz), 6.342 (d, 1H, J=1.9 Hz), 6.804 (d, 1H, J=8.2 Hz), 6.866 (d, 1H, J=8.2 Hz), 6.969–7.042 (m, 3H), 9.138 (s, 1H), 11.682 (s, 1H).

EXAMPLE 2

Silibinin-7-oleate

The synthesis of Silibinin-7-oleate was performed in the same manner as in Example 1. Obtained: 0.74 g (48% yield) of Silibinin-7-oleate.

Spectroscopic Data of Silibinin-7-oleate

Electro-spray mass spectrum in the negative scan showed: m/z 745 [M–H] $^1$H-NMR (500 MHz, DMSO-d$_6$) δ: 0.839 (t, 3H, J=6.7 Hz), 1.226–1.277 (br, 24H), 1.597 (m, 2H), 1.976 (br, 4H), 2.541 (t, 2H, J=7.2 Hz), 3.543 (m, 1H), 3.776 (s, 3H), 4.170 (br, 1H), 4.770 (m, J=5.8 Hz), 4.913 (d, 1H, J=7.8 Hz), 4.955 (t, 1H, J=5.4 Hz), 5.224 (d, 1H, J=11.6), 5.316 (m, 2H), 5.959 (d, 1H, J=6.5 Hz), 6.298 (d, 1H, J=2.4 Hz), 6.340 (d, 1H, J=1.6 Hz), 6.800 (d, 1H, J=8.0 Hz), 6.863 (d, 1H, J=8.0 Hz), 6.968–7.037 (m, 3H), 7.104 (d, 1H, J=1.9 Hz), 9.144 (s, 1H), 11.683 (s, 1H).

EXAMPLE 3

Silibinin-7-phosphate and silibinin-17-phosphate

To a stirred solution of silibinin (0.48 g, 1 mmol) and di-tert-butyl diisopropylphosphoramidite (0.315 ml, 1 mmol) in N,N-dimethylacetamide (2 ml) added 1H-tetrazole (420 mg, 6 mmol). After 15 min the reaction mixture was cooled to −10° C. and a solution of 3-chloroperoxybenzoic acid (0.4 g) in 2 ml dichloromethane was added gradually. The reaction mixture was stirred for 15 min and the diluted in ethyl acetate. The organic phase was washed with 10% $Na_2S_2O_5$, 1N HCl, 5% $Na_2CO_3$ and water. After removal of the solvent the crude product was separated on silica gel column using chloroform/ethyl acetate/ethanol (10:1:0.5) as a solvent system. Two major fractions were obtained, which were separately hydrolyzed in 30% trifluoroacetic acid in acetic acid for 1 h at room temperature. After removal of the acids under high vacuum, each residue was dissolved in methanol and neutralized with 1N NaOH to pH 8.5. Obtained resides after evaporation of methanol were crystallized from ethanol. Obtained: 0.195 g (33% yield) of silibinin-7-phosphate sodium salt and 0.098 g (17%) of silibinin-17-phosphate sodium salt.

Spectroscopic Data of Silibinin-7-phosphate monosodium salt

Electro-spray mass spectrum in the negative scan showed: m/z 561 [M–Na] and 583 [M-H]. $^{31}$P-NMR (500 MHz, D$_2$O) δ: −0.0129.

Spectroscopic Data of Silibinin-17-phosphate monosodium salt

Electro-spray mass spectrum in the negative scan showed: m/z 561 [M–Na] and 583 [M-H]. $^{31}$P-NMR (500 MHz, D$_2$O) δ: 0.1153.

REFERENCES

1) Lotter, H. and H. Wagner. *Z. Naturforsch.* 38c:339–341, 1983.
2) Bhatia, N., Zhao, J. F., Wolf, D. M. and R. Agarwal. *Cancer Letters* 147:77–84, 1999.

3) Zhao, J. F. and R. Agarwal. *Carcinogenesis* 20(11):2101–2108, 1999.
4) Mowrey, D. B. *Next Generation Herbal Medicine.* Keats Publishing, Inc., New Canaan, Conn., 1990. Pp. 108–126.
5) Saliou, C., Rihn, B., Cillard, J., Okamoto, T. and L. Packer. *FEBS Letters* 440:8–12, 1998.
6) Zi, X. L., Feyes, D. K. and R. Agarwal. *Clinical Cancer Research* 4:1055–1064, 1998.
7) Zi, X. L., Grasso, A. W., Kung, H. J. and R. Agarwal. *Cancer Research* 58:1920–1929, 1998.
8) Lahiri-Chatterjee, M., Katiyar, S. K., Mohan, R. R. and R. Agarwal. Cancer research 59:622–632, 1999.
9) Katiyar, S. K., Korman, N. J., Mukhtar, H. and R. Agarwal. *Journal of the National Cancer Institute* 89(8):556–566, 1997.
10) Zi, X. L., Sharma, Y., and R. Agarwal. *Molecular Carcinogenesis* 26:321–333, 1999.
11) Bonne, C. and D. Sincholla. U.S. Pat. No. 4,749,573, 1988.
12) Papaconstantin, E., Lepage, P. Frelejouand, L. P. and J. P. Marty. U.S. Pat. No. 4,997,649, 1991.
13) Bombardelli, E. U.S. Pat. No. 4,895,839, 1990.
14) Bortolin, V. EP No. EP 0552439A1, 1992.
15) Schreiner, E. DE No. DE4322614, 1995.
16) Gabetta, B., Bombardelli, E. and G. Pifferi. U.S. Pat. No. 4,764,508, 1988.
17) Ely, P. H. U.S. Pat. No. 5,196,448, 1993.
18) Perich, J. W. and R. B. Johns. A New, Convenient and Efficient General Procedure for the Conversion of Alcohols into Their Dibenzyl Phosphorotriesters Using N,N-Diethyl Dibenzyl Phosphoramidite. *Tetrahedron Letters* 28:101–102, 1987.
19) Perich, J. W. and R. B. Johns. Di-t-Butyl N,N-Diethylphosphoramidite and Dibenzyl N,N-Diethylphosphoramidite. Highly Reactive Reagents for the "Phosphite-Triester" Phosphorylation of Serine-Containing Peptides. *Tetrahedron Letters.* 29:2369–2372, 1988.

Readers of skill in the art to which this invention pertains will understand that the foregoing description of the details of preferred embodiments is not to be construed in any manner as to limit the invention. Such readers will understand that other embodiments may be made which fall within the scope of the invention, which is defined by the following claims and their legal equivalents.

What is claimed is:

1. A hydrophilic silibinin pro-form of the formula

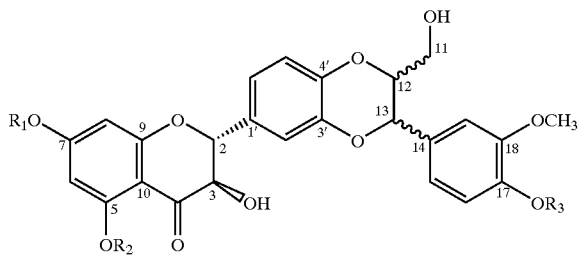

wherein
one or more of $R_1$, and $R_2$, and $R_3$ are independently selected from the group consisting of cationic esters, anionic esters, neutral esters, and H.

2. A pharmaceutical composition suitable for topical or oral administration in an individual, said composition comprising a hydrophilic silibinin pro-form and a pharmaceutically acceptable carrier, wherein said silibinin pro-form has the formula:

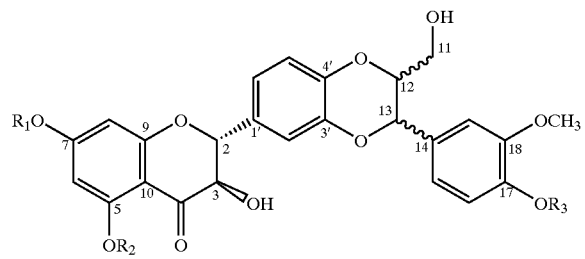

wherein
one or more of $R_1$, and $R_2$, and $R_3$ are independently selected from the group consisting of cationic esters, anionic esters, neutral esters, and H.

3. A lipophilic silibinin pro-form of the formula

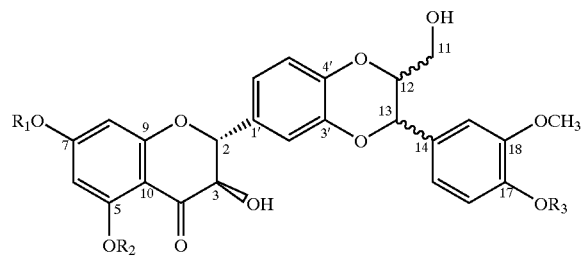

wherein
one or more of $R_1$, and $R_2$, and $R_3$ are independently selected from the group consisting of aliphatic acid residues, aromatic acid residues, and H.

4. The lipophilic silibinin pro-form of claim 3 wherein said aliphatic ester comprises saturated or unsaturated, linear or branched, carboxylic residue having from 2 to 30 carbon atoms or an aliphatic ester composed of saturated or unsaturated, linear or branched, carboxylic residue having from 2 to 30 carbon atoms substituted with oxygen, sulfur or nitrogen functional groups.

5. The lipophilic pro-form of claim 3 wherein said esters are saturated or unsaturated fatty acid residues having from 10 to 30 carbon atoms.

6. A pharmaceutical composition suitable for topical or oral administration in an individual, said composition comprising a lipophilic silibinin pro-form and a pharmaceutically acceptable carrier, wherein said silibinin pro-form has the formula:

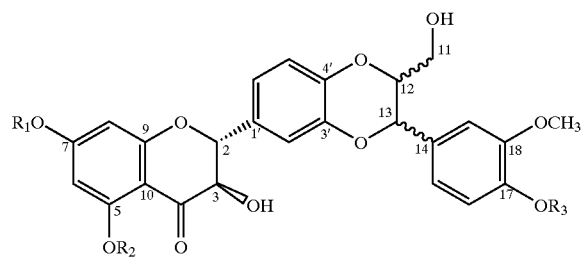

wherein
one or more of $R_1$, and $R_2$, and $R_3$ are independently selected from the group consisting of aliphatic acid residues, aromatic acid residues, and H.

7. The lipophilic silibinin pro-form of claim 5 wherein said aliphatic ester comprises saturated or unsaturated, linear or branched, carboxylic residue having from 2 to 30 carbon atoms or an aliphatic ester composed of saturated or unsaturated, linear or branched, carboxylic residue having from 2 to 30 carbon atoms substituted with oxygen, sulfur or nitrogen functional groups.

8. The lipophilic pro-form of claim 6 wherein said esters are saturated or unsaturated fatty acid residues having from 10 to 30 carbon atoms.

9. A method of treating a subject having or at risk of having a cell proliferative disorder, said method comprising administering to the subject a therapeutically effective amount of a silibinin pro-form.

10. The method of claim 8 wherein said silibinin pro-form is a hydrophilic pro-form.

11. The method of claim 8 wherein said silibinin pro-form is a lipophilic pro-form.

12. The method of claim 8 wherein said cell proliferative disorder is selected from the group consisting of breast cancer, skin cancer, uterine cancer, testicular cancer, lung cancer, prostate cancer, and liver cancer.

13. A method of decreasing oxidative stress in a subject having a disorder associated with oxidative stress, said method comprising administering to the subject a therapeutically effective amount of a silibinin pro-form.

14. The method of claim 12 wherein said disorder is selected from the group consisting of diabetes, cerebral anemia, and pelioma.

15. A method of treating a subject having or at risk of having a disorder associated with sebaceous gland activity, said method comprising adminstering to the subject a therapeutically effective amount of a silibinin pro-form.

16. The method of claim 14 wherein said disorder is selected from the group consisting of increased sebum production, acne of the skin, and acne of the scalp.

17. A method of treating a subject having or at risk of having a cardiovascular disorder, said method comprising administering to the subject a therapeutically effective amount of a silibinin pro-form.

18. The method of claim 16 wherein said cardiovascular disorder is selected from the group consisting of atherosclerosis and hypercholesteremia.

\* \* \* \* \*